United States Patent [19]
Cavazza et al.

[11] Patent Number: 5,639,767
[45] Date of Patent: Jun. 17, 1997

[54] THERAPEUTICAL METHOD FOR TREATING DERMATOSES BASED ON THE USE OF O-ESTERS OF L-CARNITINE WITH AROMATIC ACIDS

[75] Inventors: Claudio Cavazza; Paolo Cavazza, both of Rome, Italy

[73] Assignee: Avantgarde S.p.A., Rome, Italy

[21] Appl. No.: 253,051

[22] Filed: Jun. 2, 1994

[30] Foreign Application Priority Data

Jun. 2, 1993 [IT] Italy .................. RM93A0365

[51] Int. Cl.⁶ .................................. A61K 31/44
[52] U.S. Cl. ............................ 514/351; 514/731
[58] Field of Search ....................... 514/533, 351, 514/731

[56] References Cited

PUBLICATIONS

Meul 116 CA:214911k 1992.
Knoll et al 106 CA:72696m 1987.

*Primary Examiner*—Russell Travers
*Attorney, Agent, or Firm*—Oblon, Spivak, McClelland, Maier & Neustadt, P.C.

[57] ABSTRACT

The use of O-esters of L-carnitine with aromatic acids, such as salicylic, acetylsalicylic, nicotinic and trimethoxybenzoic acid is disclosed for producing pharmaceutical compositions suitable to be topically applied for treating dermatoses, such as ichthyosis and psoriasis.

7 Claims, No Drawings

THERAPEUTICAL METHOD FOR TREATING DERMATOSES BASED ON THE USE OF O-ESTERS OF L-CARNITINE WITH AROMATIC ACIDS

The present invention relates to the use of O-esters of L-carnitine with aromatic acids for producing pharmaceutical compositions which contain such esters as active ingredients, suitable to be topically applied for the treatment of dermatoses.

These esters have the formula (I)

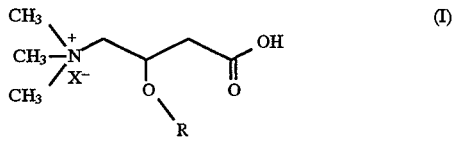

wherein

R is the acyl of an aromatic acid, and $X^-$ is the anion of a pharmacologically acceptable acid.

Specifically, the esters which are particularly preferred are those wherein the acid is selected from salicylic acid, acetylsalicylic acid, nicotinic acid and trimethoxy benzoic acid.

Encompassed by the esters to be used according to the present invention are also the inner salts of the compounds of the formula (I).

Pharmaceutically acceptable salts of the compound of formula (I) include, in addition to the inner salts, all pharmaceutically acceptable salts which are prepared by the addition of acid to L-carnitine, and which do not give rise to undesirable toxic or collateral effects. The formation of pharmaceutically acceptable acid addition salts is well known in pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulfate, glucose, phosphate, tartrate and acid tartrate salts.

The esters of the formula (I) wherein the acyl group is derived from salicylic acid and acetylsalicylic acid, i.e. salicyloyl L-carnitine and acetylsalicyloyl L-carnitine, are known compounds. Specifically: salicyloyl L-carnitine is disclosed in CH 679 856, and acetylsalicyloyl L-carnitine is disclosed in CH 679 395. Both carnitine esters possess analgesic activity.

Also nicotinoyl carnitine is a known compound, see FR 2354769 wherein its hypolipidaemic activity is disclosed.

All the aforesaid patents are incorporated herein by reference.

The dermatoses which are suitably treated with the compositions of the present invention are in particular ichthyosis, psoriasis and those dermatoses which are induced by a defective keratinization, such as dandruff, acne and palmar and plantar hyperkeratosis.

Ichthysosis is a dermatosis characterized by generalized dryness, harshness and scaling of the skin. It may occurs as a hereditary disease present at birth, or as a metabolic disorder associated with hypothyroidism or with the intake of drugs (such as butyrophenols) inhibiting lipid synthesis, or as a paraneoplastic syndrome, manifestation of a tumor process involving internal organs.

Xeroderma, the mildest form of ichthyosis is neither congenital nor associated with systemic abnormalities. It usually occurs on the lower legs of middle-aged or older patients, most often in cold weather and in patients who bathe frequently. There may be mild to moderate itching and an associated dermatitis due to detergents or other irritants.

The inherited ichthyoses, all characterized by excessive accumulation of scale on the skin surface, are classified according to clinical, genetic, and histologic criteria.

Known treatments of any form of ichthyosis comprise topically applying to the skin hydrating emollients. Furthermore, salicylic acid or vitamin A-containing ointments have been widely used.

A keratolytic agent particularly effective in removing the scale in ichthyosis vulgaris, lamellar ichthyosis and sex-linked ichthyosis contains 6% salicylic acid in a gel composed of propylene glycol, ethyl alcohol, hydroxypropylene cellulose and water.

Further known drugs for the treatment of this disorder include: 50% propylene glycol in water, hydrophilic petrolatum and water (in equal parts), and cold cream and an $\alpha$-hydroxy acid (e.g. lactic and pyruvic acid) in various bases. In lamellar ichthyosis, 0,1% tretinoin (vitamin A acid: retinoic acid) cream has been utilized. None of these treatments has been found satisfactorily effective.

Hyperkeratosis is a thickening of the stratum corneum of the skin.

The treatment of choice is the topical application of drugs containing urea, propylene glicol or salicylic acid. Also in this case, none of the known treatment has proved to be satisfactorily effective.

It has now been found that the compounds of the present invention, when topically applied as solutions, lotions, creams or ointments containing from 0,01% to 20%, preferably from 1% to 15% and most preferably from 2 to 10% by weight of at least one of the foregoing compounds, are potently effective in achieving complete remission of ichthyotic conditions in humans and in healing psoriasis and those disorders brought about by an altered keratinization, such as dandruff, acne and palmar and plantar hyperkeratosis.

It has also been found that, if the solutions, creams or ointments of the invention are applied regularly on a daily basis, within about two to three weeks the effected skin areas will return to norm conditions.

In order to prepare the compositions of this invention, at least one of the compounds of the formula (I) is preferably dissolved in water or ethanol initially. The solution thus prepared may be admixed in the conventional manner with commonly available ointment bases such as hydrophilic ointments (USP) or petrolatum (USP).

The water or ethanol used to dissolve the compounds according to this invention may range in concentration of from 1 to 30%, by volume, of the total composition. The compounds of this invention may also be formulated in a solution or lotion form.

For instance, a compound of the formula (I) is dissolved directly in a mixture of water, ethanol and propylene glicol (40:40:20 by weight).

Some examples of formulation are hereinbelow described:

Formulation 1: 5% solution 5 grams of a compound of the formula (I) were dissolved in 5 mL of water and the resulting solution admixed with 40 mL of ethanol and 20 mL of propylene glycol. Sufficient water was added to make 100 mL of formulation.

Formulation 2: 5% ointment 5 grams of a compound of the formula (I) were admixed with 95 grams of USP grade hydrophilic ointment, until a uniform consistency resulted.

What is claimed is:

1. A therapeutical method for treating dermatoses which comprises topically applying to the skin of a patient in need thereof a dermatologically effective amount of an L-carnitine ester having the formula (I)

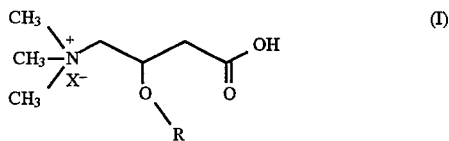

wherein

R is the acyl group of an aromatic acid selected from the group consisting of nicotinic acid and trimethoxybenzoic acid, and $X^-$ is the anion of a pharmacologically acceptable acid.

2. The method of claim 1 which comprises topically applying a pharmaceutical composition comprising from 0,01% to 20% by weight of an ester of formula (I) and a pharmacologically acceptable excipient.

3. The method of claim 2, which comprises topically applying a pharmaceutical composition comprising from 1% to 15% by weight of an ester of formula (I) and a pharmacologically acceptable excipient.

4. The method of claim 3, which comprises topically applying a pharmaceutical composition comprising from 2% to 10% by weight of an ester of formula (I) and a pharmacologically acceptable excipient.

5. The method of claim 1 for treating ichthyosis and psoriasis.

6. The method of claim 1 for treating dermatoses brought about by defective keratinization.

7. The method of claim 1 for treating dandruff, acne and palmar and plantar hyperkeratosis.

* * * * *